US00PP14302P39

(12) United States Plant Patent
Miyazaki

(10) Patent No.: US PP14,302 P3
(45) Date of Patent: Nov. 18, 2003

(54) TORENIA PLANT NAMED 'SUNRENIRIREPA'

(50) Latin Name: *Torenia hybrida*
Varietal Denomination: cv. Sunreniririrepa

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/066,739

(22) Filed: Feb. 6, 2002

(65) Prior Publication Data

US 2003/0150033 P1 Aug. 7, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,118 P 11/1997 Miyazaki et al.
PP10,119 P 11/1997 Nagase
PP10,120 P 11/1997 Nagase
PP10,843 P 3/1999 Tamura et al.
PP11,131 P 11/1999 Miyazaki
PP12,105 P2 9/2001 Miyazaki

OTHER PUBLICATIONS

UPOV–ROM GTITM Computer Database 2000/04, Aug. 16, 2000, GTI Jouve Retrieval Software, Citation for Torenia 'Sunreniririrepa'.*
Official Gazette of Japan, two pages (Mar. 18, 1999).
Flower & Green 2001 Catalog, Cover page plus two pages (Oct. 2000).
Euro American Catalog, 2001–2002 Plant Collection, Cover page plus one page (about Oct. 2001).

* cited by examiner

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

Disclosed herein is a Torenia plant which displays large globose flowers having vivid red purple petals and a vivid red purple floral tube. The plant has a semi-erect growth habit and medium branching. A great profusion of blooms is formed with the entire plant remaining in bloom for a considerable period of time.

2 Drawing Sheets

Figure 1:
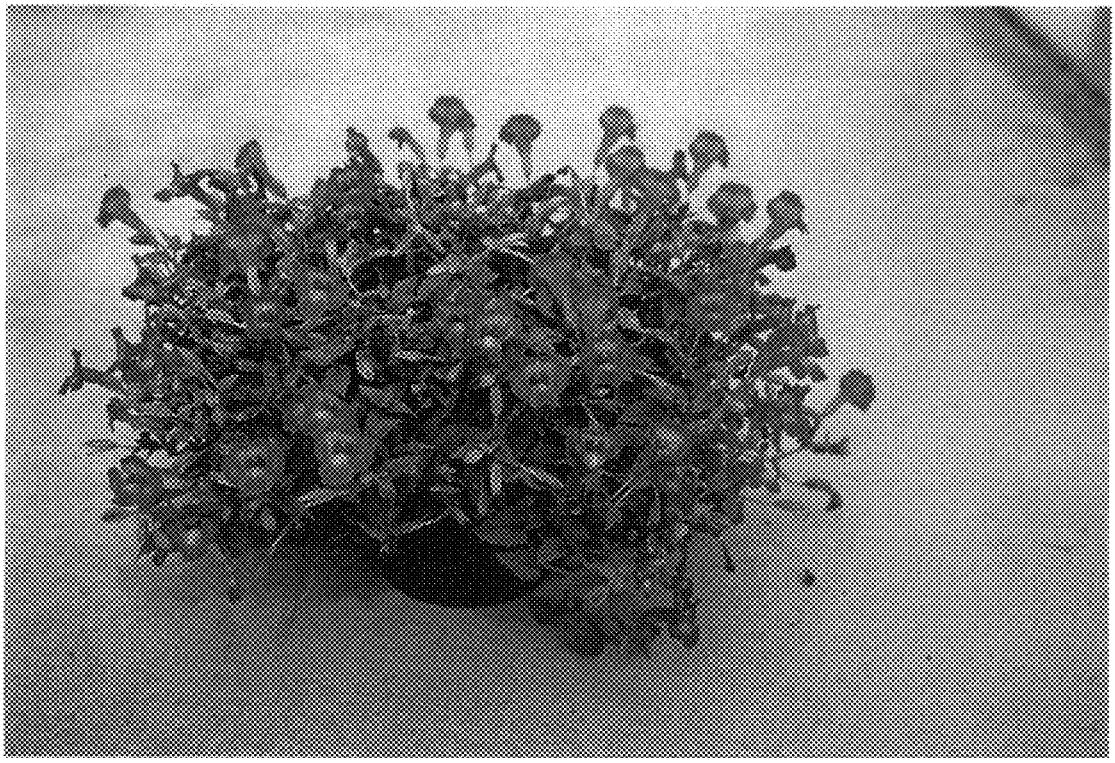

Botanical/commercial classification: Torenia hybrida/ Torenia Plant.
Varietal denomination: cv. Sunreniririrepa.

BACKGROUND OF THE VARIETY

The present invention relates to a new and distinct variety of Torenia plant that was obtained as a spontaneous mutation of unknown causation of the 'Sunrenimu' variety (U.S Plant Pat. No. 10,120).

The Torenia is a very popular plant and is used for flower bedding and potting in the summer season. There are only a few varieties of the Torenia plant which have a semi-erect growth habit, medium branching, and a great profusion of blooms.

Accordingly, this invention is aimed at obtaining a new variety having vivid red purple flower petals without a yellow eye color, a semi-erect growth habit, medium branching, and great profusion of blooms.

The new variety of Torenia plant was discovered during January 1997 primarily on the basis of the distinctive flower color during propagation of 'Sunrenimu' variety at Yokaichi-shi, Shiga-ken, Japan. The new Torenia plant was propagated by the use of cuttings beginning in January 1997, and then was grown in flower beds and pots beginning in April 1997. The botanical characteristics of the plant were examined using a similar 'Crown Violet' variety (non-patented in the United States) and the parental variety for comparison. As a result, it was concluded that the new Torenia plant of the present invention is distinguishable from all other varieties whose existence is known to me. The new variety is uniform and stable in its characteristics has been named 'Sunreniririrepa'.

In the following description the color-coding is in accordance with The R.H.S. Colour Chart of The Royal Horticultural Society, London, England. A color chart based on The Japan Color Standard for Horticultural Plants (J.H.S. Color Chart) is also added for reference.

The 'Sunrenimu' parent plant variety was obtained from crossing the 'Crown Violet' variety having purplish white flower petals as the female parent and the 'Con Color' variety having strong bluish purple flower petals as the pollen parent. This cross was carried out during February 1993 at Shimamoto-cho, Mishima-gun, Osaka-fu, Japan.

The main botanical characteristics of 'Crown Violet' namely are as follows:

Plant:
- *Growth habit.*—Erect.
- *Plant height.*—Approximately 20–30 cm.
- *Plant width.*—Approximately 30–50 cm.

Stem:
- *Diameter.*—Approximately 3.0 mm.
- *Anthocyanin pigmentation.*—Present.
- *Branching.*—Few.
- *Pubescence.*—Sparse.
- *Length of internode.*—Approximately 1–3 cm.

Leaf:
*Phyllotaxis.*—Opposite.
*Shape of blade.*—Serrate.
*Length.*—Approximately 2.0–4.0 cm.
*Width.*—Approximately 2.0–3.0 cm.
*Depth of incision.*—Deep.
*Color.*—Dark yellow green (R.H.S. 137A, J.H.S. 3508).
*Pubescence of upper side.*—Sparse.
Flower:
*Facing direction.*—Lateral.
*Diameter.*—Approximately 2.0–3.0 cm.
*Length.*—Approximately 20–30 mm.
*Color of floral tube.*—Soft violet (R.H.S. 92C, J.H.S. 8008).
*Color of petal.*—Purplish white (R.H.S. 62D, J.H.S. 8001).
*Yellow eye color.*—Present. Vivid yellow (R.H.S. 17C, J.H.S. 2507).
*Calyx.*—Approximately 1.5–2.0 cm in length.
*Anthocyanin pigmentation of calyx limb.*—Present.
*Peduncle.*—Approximately 1.5–2.0 mm in thickness, and approximately 1.5–2.0 cm in length.
*Reproductive organs.*—1 pistil and 4 stamens.
*Anther color.*—White.
*Flowering duration.*—Medium.
Physiological and ecological characteristics: Low resistance to diseases and pests, high tolerance to heat and low tolerance to cold.
The main botanical characteristics of 'Con Color' variety are as follows:
Plant:
*Growth habit.*—Decumbent.
*Plant height.*—Approximately 10–15 cm.
*Plant extension.*—Approximately 50–70 cm.
Stem:
*Diameter.*—Approximately 1.5 mm.
*Anthocyanin pigmentation.*—Present.
*Branching.*—Many.
*Pubescence.*—Sparse.
*Length of internode.*—Approximately 4–6 cm.
Leaf:
*Phyllotaxis.*—Opposite.
*Shape of blade.*—Crenate.
*Length.*—Approximately 1.0–2.0 cm.
*Width.*—Approximately 1.0–2.0 cm.
*Depth of incision.*—Medium.
*Color* (*upper side*).—Moderate olive green (R.H.S. 137A, J.H.S. 3508).
*Pubescence of upper side.*—Sparse.
Flower:
*Facing direction.*—Lateral.
*Diameter.*—Approximately 2.0–3.0 cm.
*Length.*—Approximately 20–30 mm.
*Color of floral tube.*—Moderate purple (R.H.S. 83B, J.H.S. 8613).
*Color of petal.*—Single color; Deep purple (R.H.S. 89C, J.H.S. 8311).
*Yellow eye color.*—Absent.
*Calyx.*—Approximately 1.5–2.0 cm in length.
*Anthocyanin pigmentation of calyx limb.*—Present.
*Peduncle.*—Approximately 1.5–2.0 mm in thickness, and approximately 3.0–5.0 cm in length.
*Reproductive organs.*—1 pistil and 4 stamens.
*Anther color.*—White.
*Flowering duration.*—Medium.
Physiological and ecological characteristics: High resistance to diseases and pests, high tolerance to heat and low tolerance to cold.
The main botanical characteristics of the Torenia plant 'Sunrenimu' variety are as follows:
Plant:
*Growth habit.*—Semi-erect, the stems hang down pliantly when potted in a hanging pot.
*Plant height.*—Approximately 10–20 cm.
*Plant width.*—Approximately 50–60 cm, and the stem extends to length of approximately 60 cm from the base.
*Growth.*—Medium branching with a great profusion of blooms and the entire plant remaining in bloom for a considerable period of time.
*Blooming period.*—June to November in the southern Kanto area, Japan. The plant shape does not change throughout this period.
Stem:
*Diameter.*—Approximately 2.0 mm.
*Anthocyanin pigmentation.*—Present.
*Branching.*—Medium.
*Pubescence.*—Sparse.
*Length of internode.*—Approximately 6–8 cm.
Leaf:
*Phyllotaxis.*—Opposite.
*Shape of blade.*—Serrate.
*Length.*—Approximately 2.0–3.0 cm.
*Width.*—Approximately 1.5–2.5 cm.
*Depth of incision.*—Medium.
*Color* (*upper side*).—Moderate olive green (R.H.S. 137A, J.H.S. 3508).
*Pubescence of upper side.*—Sparse.
Flower:
*Facing direction.*—Lateral.
*Diameter.*—Approximately 2.0–3.0 cm.
*Length.*—Approximately 30–40 mm.
*Color of floral tube.*—Light purple (R.H.S. 92B, J.H.S. 8303).
*Color of petal.*—Single color, dark reddish purple (R.H.S. 83B, J.H.S. 8909).
*Yellow eye color.*—Absent.
*Calyx.*—Approximately 1.5–2.0 cm in length.
*Anthocyanin pigmentation of calyx limb.*—Present.
*Peduncle.*—Approximately 1.5–2.0 mm in thickness, and approximately 2.0–3.0 cm in length.
*Reproductive organs.*—1 pistil and 4 stamens.
*Anther color.*—White.
*Flowering duration.*—Medium.
Physiological and ecological characteristics: Medium resistance to diseases and pests, high tolerance to heat and low tolerance to cold. The plant grows and has flowers commonly when grown in the shade of trees.

SUMMARY OF THE VARIETY

The new 'Sunreniriripa' plant has a semi-erect growth habit, and forms vivid red purple flower petals without a yellow eye. The new plant displays medium branching and forms a great profusion of blooms with the entire plant remaining in bloom for a considerable period of time.

The new variety the present invention has been asexually reproduced by the use of cuttings at Kitakoma-gun Yamanashi-ken, Japan. Such propagation has confirmed that the characteristics are firmly fixed and are reliably transmitted to subsequent generations.

BRIEF DESCRIPTION OF THE PHOTOGRAPHS

Figure 2:
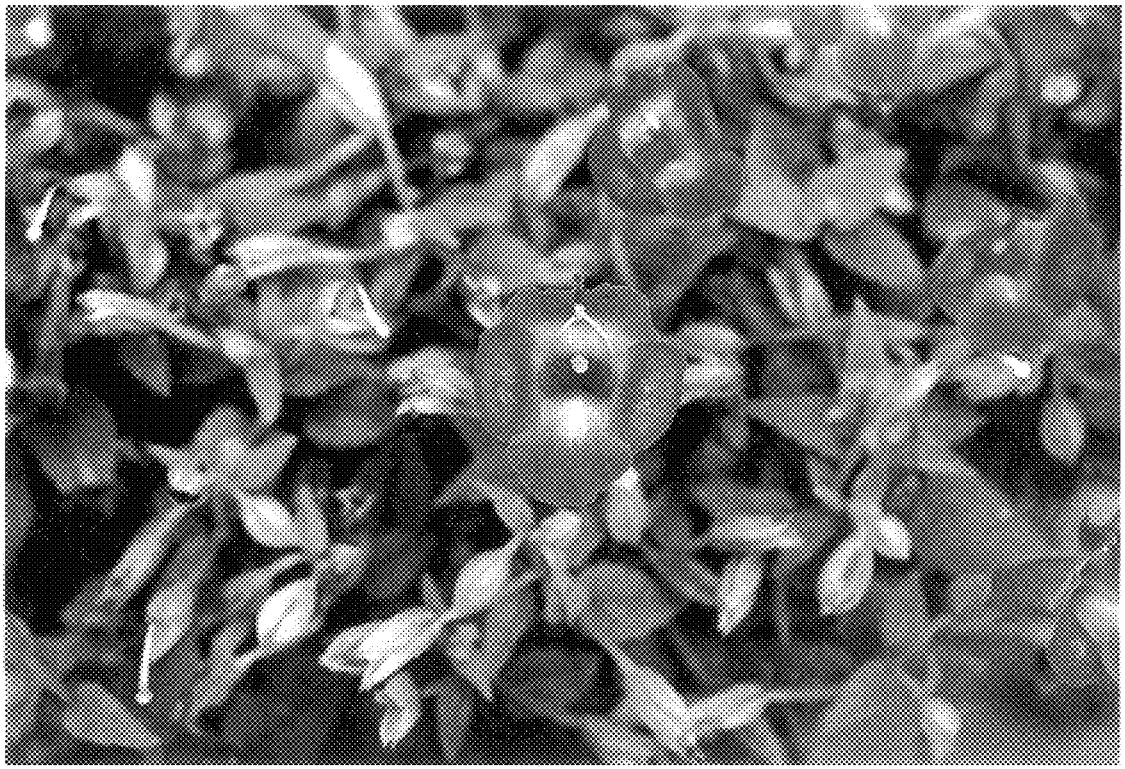

FIG. 1 shows the new variety of Torenia plant while growing in a flower pot; and FIG. 2 shows a close view of flowers and foliage of the new variety of Torenia plant.

DETAILED DESCRIPTION OF THE VARIETY

The botanical characteristics of the new and distinct variety of Torenia plant are set forth hereafter. The plants were observed at the end of July while growing at Kitakoma-gun, Yamanashi-ken, Japan. Young nursery plants were placed in a flower bed during April at a spacing of 6 plants per square meter, and in pots with 3 plants being placed in each 30 cm pot. All plants described herein were observed after approximately three months of growth.

Plant:

*Growth habit.*—Semi-erect, with the stems hanging down pliantly when potted in a hanging pot.
*Plant height.*—Approximately 20 cm.
*Plant width.*—Approximately 50 to 60 cm.
*Growth.*—Medium branching, a great profusion of blooms; the whole plant remaining in bloom for a considerable period of time.
*Blooming period.*—June to November in the southern Kanto area, Japan. The plant shape does not change throughout this period.

Stem:

*Diameter.*—Approximately 2.5 mm.
*Color.*—R.H.S. 144A.
*Anthocyanin pigmentation.*—R.H.S. 60A.
*Branching.*—Medium.
*Pubescence.*—Sparse.
*Length of internode.*—Approximately 3.1 cm.

Leaf:

*Phyllotaxis.*—Opposite.
*Shape of blade.*—Lanceolate.
*Length.*—Approximately 2.9 cm.
*Width.*—Approximately 1.9 cm.
*Margin.*—Crenate.
*Apex.*—Obtuse.
*Base.*—Truncate.
*Depth of incision.*—Medium.
*Color (upper side).*—Moderate olive green (R.H.S. 137A, J.H.S. 3508).
*Pubescence of upper side.*—Sparse.
*Thickness of petiole.*—Thick (Approximately 2.2 mm).
*Length of petiole.*—Short (Approximately 0.5 cm).

Flower:

*Inflorescence peduncles.*—Axillary.
*Flower form.*—Globose.
*Flower length.*—Medium (Approximately 28 mm).
*Flower diameter.*—Medium (Approximately 26 mm).
*Length of tube.*—Short (Approximately 22 mm).
*Color of floral tube.*—Strong reddish purple (R.H.S. 78A, J.H.S. 9208).
*Color of petal.*—Single color, strong reddish purple (R.H.S. 78A, J.H.S. 9208).
*Yellow petal eye.*—Absent.
*Color at base of petal near the throat.*—R.H.S. 76A.
*Vertical petal lines.*—Present.
*Upper bilabiate petal wave.*—Strong.
*Calyx shape.*—Shallowly five-lobed.
*Calyx degree of development of wings.*—Medium.
*Calyx length.*—Short to medium (Approximately 15 mm).
*Anthocyanin pigmentation of calyx limb.*—R.H.S. 71A.
*Stamen length.*—Approximately 13 mm.
*Filament diameter.*—Approximately 0.2 mm.
*Anthocyanin pigmentation of anther.*—R.H.S. 72B.
*Anther spur.*—Absent.
*Anther color.*—White.
*Peduncle thickness.*—Medium (Approximately 1.7 mm).
*Peduncle length.*—Short to medium (Approximately 22 mm).
*Peduncle color.*—R.H.S. 144A.
*Cluster.*—Absent.
*Number of flowers on each stem.*—Few.
*Reproductive organs.*—1 pistil and 4 stamens.
*Flowering duration.*—Medium.

Physiological and ecological characteristics: Moderate resistance to heat when compared to other Torenia varieties is displayed, the new variety has withstood temperatures as low as 5° C., displays moderate resistance to Powdery Mildew, and displays significant resistance to plant lice.

This new 'Sunreniririepa' variety is particularly suited for growing in flower beds and pots, as well as in hanging baskets.

I claim:

1. A new and distinct Torenia plant, substantially as herein illustrated and described, having the following characteristics: (A) forms large globose flowers with vivid red purple petals and a vivid red purple floral tube, (B) exhibits a semi-erect growth habit, (C) displays medium branching, and (D) forms flowers in a great profusion.

* * * * *